(12) United States Patent
Reusch

(10) Patent No.: US 6,444,975 B1
(45) Date of Patent: Sep. 3, 2002

(54) METHOD AND DEVICE FOR FERTILIZING SPECIFIC PARTIAL AREAS OF PLANTS

(75) Inventor: Stefan Reusch, Dülmen (DE)

(73) Assignee: Norsk Hydro ASA, Oslo (NO)

(*) Notice: Subject to any disclaimer, the term of this patent is extended or adjusted under 35 U.S.C. 154(b) by 0 days.

(21) Appl. No.: 09/530,768

(22) PCT Filed: Sep. 1, 1999

(86) PCT No.: PCT/DE98/02807
§ 371 (c)(1),
(2), (4) Date: Jun. 23, 2000

(87) PCT Pub. No.: WO00/13479
PCT Pub. Date: Mar. 16, 2000

(30) Foreign Application Priority Data

Sep. 3, 1998 (DE) .......................................... 198 41 991
Dec. 18, 1998 (DE) .......................................... 198 60 306

(51) Int. Cl.[7] ................................................. H01J 40/14
(52) U.S. Cl. ................ 250/222.1; 250/226; 250/559.38
(58) Field of Search ............................ 250/221.1, 226, 250/559.38, 340, 341.8, 342; 47/1.7

(56) References Cited

U.S. PATENT DOCUMENTS 4,986,665 A    1/1991   Yamanishi ................ 356/402
5,144,767 A    9/1992   McCloy et al. ............... 47/1.7
5,278,423 A  * 1/1994   Wangler et al. .......... 250/222.1
5,585,626 A   12/1996   Beck et al. .............. 250/222.1

FOREIGN PATENT DOCUMENTS

EP        0 458 107 A1    11/1991

* cited by examiner

Primary Examiner—Hung Xuan Dang
(74) Attorney, Agent, or Firm—Herbert Dubno; Jonathan Myers

(57) ABSTRACT

A method of partial area-specific-fertilization of plants which, under natural light during the fertilizer application, the chlorophyll content of the plants is ascertained by means of sensors by optical reflection measurement in the visible and near infrared spectral range, the chlorophyll content is registered and from the chlorophyll content a measurement of the nutrient state of the plant is determined and from the nutrient state of the plants a computer controls the fertilizer quantity to be applied, characterized in that the reflection measurements are taken simultaneously as inclined measurements with respect to the nadir with measurement devices oriented oppositely to one another free from shadows with light guides an the influence of the solar azimuth angle is eliminated by detecting the noise signals from all measurement directions.

15 Claims, 4 Drawing Sheets

US 6,444,975 B1

METHOD AND DEVICE FOR FERTILIZING SPECIFIC PARTIAL AREAS OF PLANTS

Figure 1:
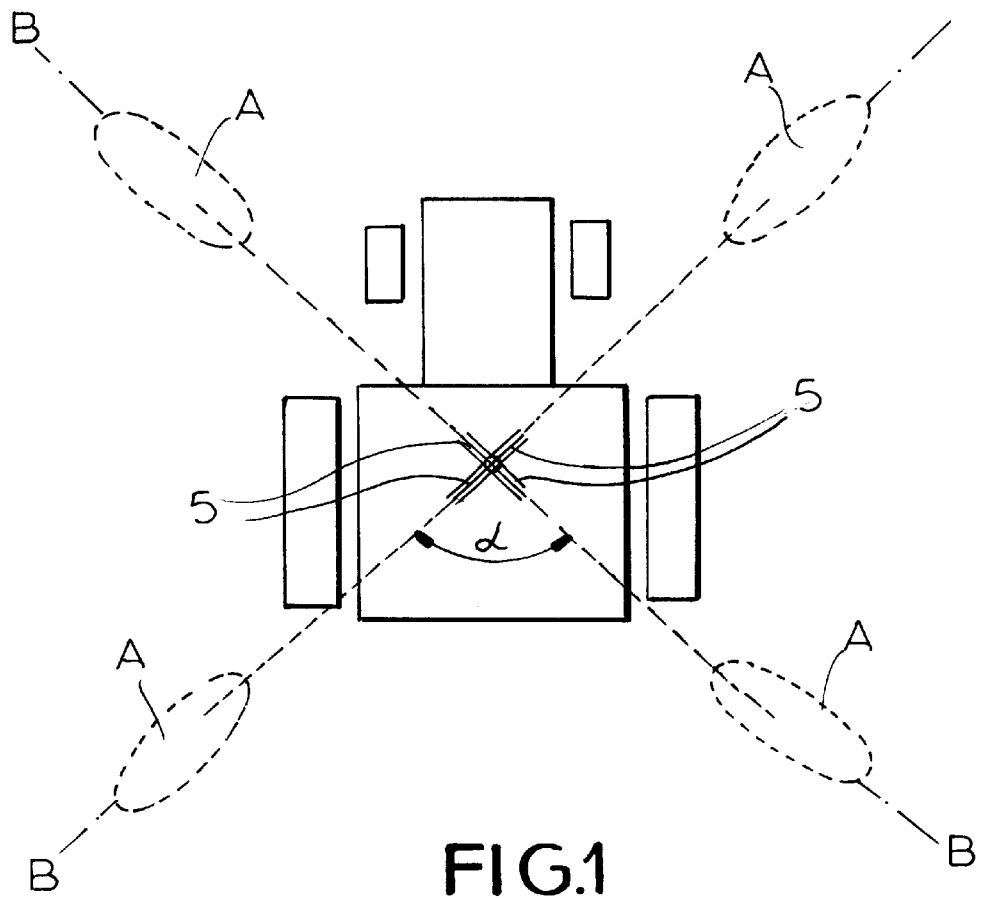

The invention relates to a method for the partial-area-specific fertilization of plants in which, by means of sensors, the chlorophyll content of the plants is determined by optical reflection measurement in the visible and near-infrared spectral ranges, the chlorophyll content is registered and from it the amount of nutrients required for the plants is determined and the corresponding fertilizer quantity to be applied is controlled by a computer.

The invention relates further to an apparatus for the partial-area-specific fertilization of plants having a displaceable carrier, especially a vehicle, which is equipped with an evaluating unit, a dispenser on the rear of the carrier for variable distribution of the fertilizer and a light waveguide affixed to the carrier and directed onto the plant stock in the direction of travel of the advancing carrier and connected with a spectrometer for spectral analysis of the reflected radiation and which supplies the reflection data for evaluation to the evaluation unit.

It is known to determine the nutrient state of plants taking into consideration their chlorophyll contents ("Precise" brochure of Hydro Agri, 1997). The chlorophyll content is customarily ascertained by means of optical reflection sensors as has been basically described in U.S. Pat. No. 4,986,665.

The spectral reflection data recovered is obtained in all known solutions operating with natural light hitherto always in a vertical incidence position from above. Inclined pick-up angles result in an influence upon the reflection spectra by the solar azimuth angle and thus a falsification of the measurement results. Defined measurement conditions are thus very difficult to maintain.

The maintenance of the vertical incidence position requires, in addition, extraordinarily expensive structures for mounting the light guides on the displaceable carrier so as to pass the light guides with a sufficient spacing outside of the shadow region of the carrier above the plant stock. So that a sufficiently large area of the stock can be sensed, a plurality of expensive light guides are affixed on the carrier and are attached to bars articulated to swing out in the width direction.

Because of the outwardly swung bars, the maneuverability of the carrier/vehicle on the field is limited and there is a danger of running into obstructions.

In this state of the art the invention sets forth the object of so improving a method and device of the type described at the outset that in spite of an inclined measurement, the effect of the solar azimuth remains excluded and the robustness and compactness of the measurement system is increased while at the same time the vehicle or carrier can be serviced more simply.

These objects are achieved by a method of the kind set forth at the outset with the characterizing features of claim 1 and by a device with the characterizing features of claims 5 and 9. Advantageous configurations of the method and the device are deducible from the dependent claims.

The method of the invention enables the chlorophyll content of the plants to be determined as a measure of their nutrient state in an optical reflection inclined scan without an effect of the solar azimuth angle on the measurement results and thus the usable to noise signal ratio is reduced [sic].

The device of the invention for carrying out the method has the advantage of a compact and robust construction with simultaneously simpler serviceability.

With all of these features it is possible to better achieve the solution according to the invention of the complex requirements of a partial-area-specific fertilization with high efficiency and precision.

Further advantages and details are given in the following description with reference to the accompanying drawing.

The invention is described further in terms of two embodiments below.

Figure 2:
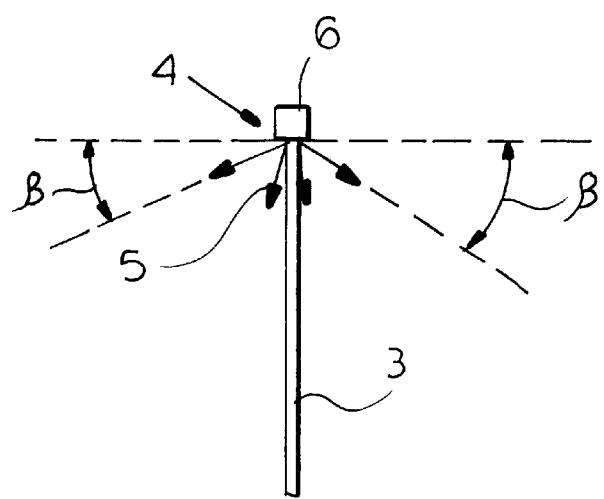
Figure 3:
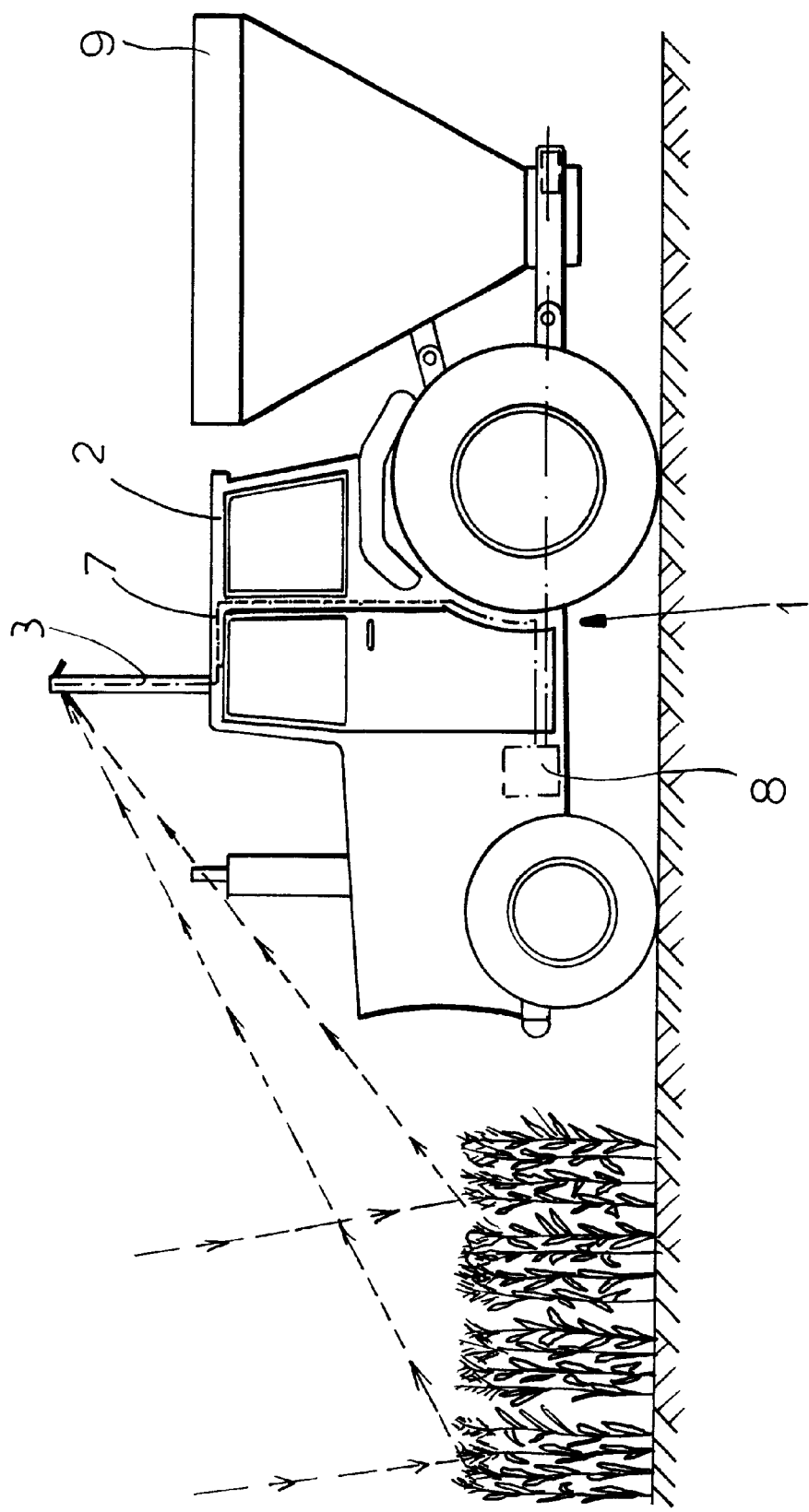
Figure 4:
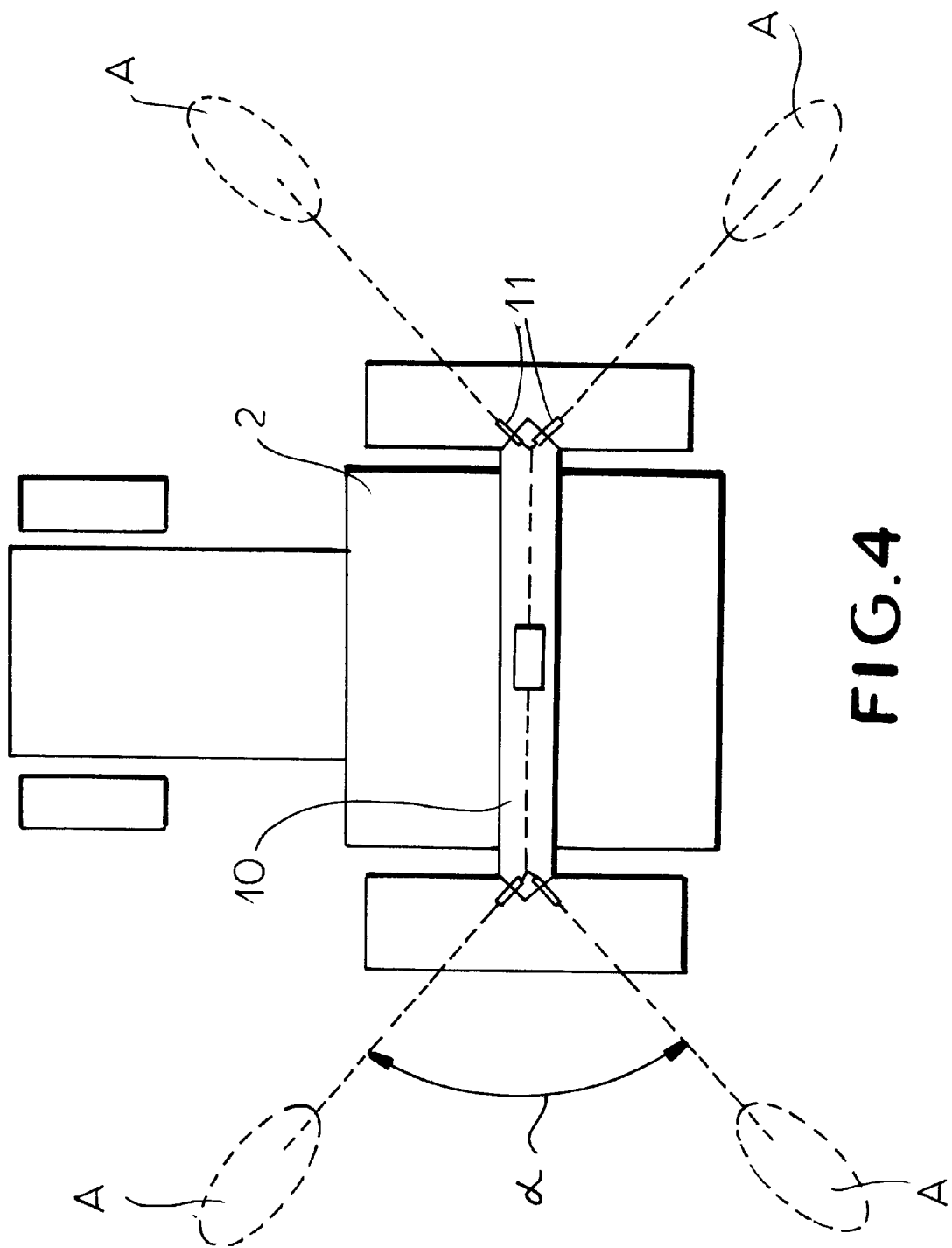
Figure 5:
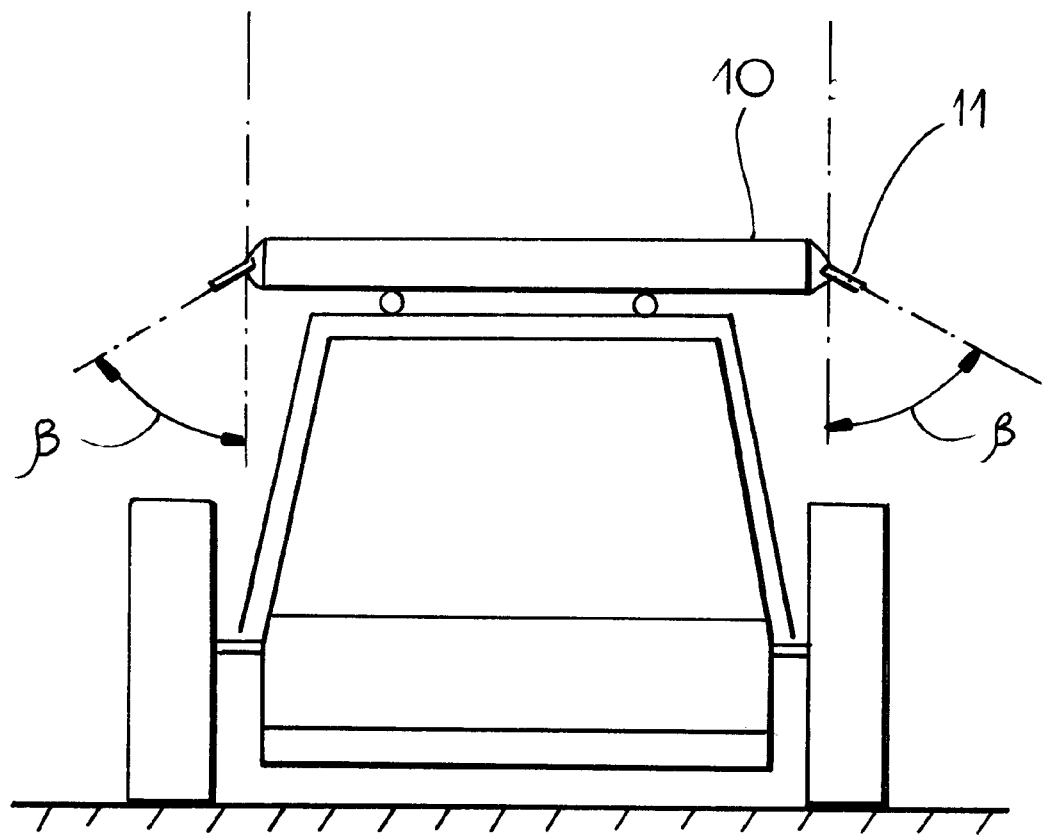

They show:

FIG. 1 a schematic elevational view of an agricultural vehicle with a sensor arrangement fastened above its roof, FIG. 2 a schematic illustration of the mast with the sensor arrangement, FIG. 3 a side elevational view of the vehicle showing the evaluation unit and dispenser, FIG. 4 a further variant of a device according to the invention with a sensor arrangement affixed laterally on the roof in a plan view and FIG. 5 an elevational view of the rear side according to FIG. 4.

EXAMPLE 1

FIG. 1 shows a tractor 1 as a carrier and on the roof 2 of which a mast 3 of relatively short length, for example, 0.8 m, is fastened. At the upper end 4 of this mast 3 there are four light conductors 5 (coupling points) which in plan view are shown to include an angle $\alpha$ of 90° with respect to one another. Each of the light conductors 5 is inclined at an angle $\beta$ (angle to the nadir) of 62° with respect to the plant stock. Naturally on the end 4 of the mast 3, a diffuser 6 is affixed to avoid the influence of ambient light.

The individual light guides 5 sense a measurement area A which lies laterally ahead and behind the tractor 1. These measurement surfaces A are schematically shown in FIG. 1 as four ellipses. Each two light guides 5 lie positively directed on an effective line B—B of several light guide pairs, for example four light guides 5, lie perpendicular to one another. All coupling points are thus spaced equidistantly from one another.

A light guide 7 extends along the mast 3 and at the end 4 of the mast 3 to form the coupling points, is split four-fold and forms the light guides 5. Each light guide is associated with a spectrometer not shown for the reflected radiation and a spectrometer for the solar radiation as required (see FIG. 2).

Because of the symmetrical arrangement of the coupling points at 90°, a substantial independence of the acquired signal from the solar azimuth angle is achieved since for each of the light guides 5 the sun always shines from the rear, left, front and right. Effects based upon the azimuth angle between the sun and the light guide and thus the effect on the signal from all four directions cancel. Size and distance of the measurement area A from the vehicle track can be so selected that the measurement area lies outside the shadow region of the tractor. In the present case, at a height of 4.5 m above the ground, an aperture angle of the fiber of 12° and the aforementioned acquisition angle of 62°, a 4 m wider strip left and right of the center line of the travel path can be sensed. The inner edges of these strips lie sufficiently far from the shadow region of the tractor. The reflected radiation acquired by the light guides 5, as shown in FIG. 3, is supplied to the evaluating device 8 in which the chlorophyll content of the plants is determined and controlled. The dispenser 9 has a measure and nutrient state via the onboard computer.

EXAMPLE 2

In FIGS. 4 and 5 a further variant of the sensor arrangement mounting according to the invention has been shown.

On the roof 2 of the carrier, cantilevered support arms 10 are affixed transverse to the travel direction and on both sides of the roof 2 of the carrier. The support arms 10 carry at their respective front ends, two swingably adjustable light guide ends 11 which are oriented preferably at an angle β of 60° (inclined position) to the plant stock. Both light guide ends 11 include an angle α with one another of 90°.

| The Significance of the Reference Characters Used | |
|---|---|
| Tractor | 1 |
| Roof | 2 |
| Mast | 3 |
| Upper end of 3 | 4 |
| Light guide (coupling points) | 5 |
| Diffuser | 6 |
| Light guide | 7 |
| Evaluating device | 8 |
| Dispenser | 9 |
| Support arms | 10 |
| Light guide end | 11 |
| Measurement area | A |
| Effective line | B—B |
| Angle between effective lines or the light guide ends | α |
| Acquisition angle (angle to the nadir) or inclination | β |
| 5 Sheets of Drawing Attached | |

What is claimed is:

1. A method of partial area-specific-fertilization of plants which, under natural light during the fertilizer application, the chlorophyll content of the plants is ascertained by means of sensors by optical reflection measurement in the visible and near infrared spectral ranges, the chlorophyll content is registered and from the chlorophyll content a measurement of the nutrient state of the plant is determined and from the nutrient state of the plants a computer controls the fertilizer quantity to be applied, characterized in that the reflection measurements are taken simultaneously as inclined measurements with respect to the nadir with measurement devices oriented oppositely to one another free from shadows with light guides and the influence of the solar azimuth angle is eliminated by detecting the noise signals from all measurement directions.

2. The method according to claim 1, characterized in that the inclined measurement is carried out in at least four measuring devices whereby the number of measurement devices is an even number.

3. The method according to claim 2, characterized in that the inclined measurement is carried out additionally with artificial lighting.

4. The method according to claim 1, characterized in that the inclined measurement is carried out from a plurality of superposed plants whereby the angular position of the nadir differs from plane to plane.

5. A device for the partial-area-specific fertilization of plants for carrying out the method according to claim 1 with a displaceable carrier which is equipped with an evaluating device, a dispenser on the rear of the carrier for variable distribution of the fertilizer and affixed to the carrier trained advancingly on the plant stock in the travel direction of the carrier and connected with a spectrometer for spectral analysis of the reflected radiation which supplies the reflection data for evaluation of the evaluating device, characterized in that the light guide is held in a raised position with respect to the carrier which is moved with the carrier and is so oriented at an inclined direction with respect to the plant stock and has two light guides oriented opposite one another or along a common effective line and the effective lines are spaced from one another by the same angle a included between them, whereby the measurement areas (A) scanned by the light guides (5) continuously lie outside the shadow region of the carrier and in that the light guides (5) in the raised position have a dispenser (6) for balancing out the ambient light input.

6. The device according to claim 5, characterized in that the inclined orientation (β) of the light guides (5) amounts to 50° to 75°, preferably 62°.

7. The device according to claim 5, characterized in that the angle (α) is preferably 30° to 90°.

8. The device according to claim 5, characterized in that the light guide (5) is oriented in a plurality of planes lying one above another whereby the inclined position (β) of all light guides in one plane differs from the inclined orientation (β) of all light guides (5) in another plane.

9. The device according to claim 5, characterized in that the light guides (5) are attached on the roof of the carrier or on other structures affixed to the carrier or on a mast (3) affixed thereto.

10. The device according to claim 5, characterized in that the light guides (5) are formed from a light guide (7) split into a multiplicity, preferably four-fold of light guides.

11. The device according to claim 5, characterized in that light guides (5) and the diffuser (6) each are associated with a respective spectrometer.

12. The device according to claim 5, characterized in that the aperture angle of the fiber of the light guide (7) is 5° to 15°, preferably 12°.

13. A device for the partial-area-specific fertilization of plants for carrying out the method according to claim 1 with a displaceable carrier, which is equipped with an evaluating device, a dispenser on the rear of the carrier for variable distribution of the fertilizer and affixed to the carrier trained advancingly on the plant stock in the travel direction of the carrier and connected with a spectrometer for spectral analysis of the reflected radiation which supplies the reflection data for evaluation of the evaluating device, characterized in that the light guide (5) is elevated above the carrier and movable with the carrier and oriented at an inclined angle (β) with respect to the plant stock such that each two light guide ends cantilevered laterally from the vehicle roof with the inclined orientation (β) include a common angle (α) with one another whereby the measurement areas (A) scanned by the light guides (5) are continuously outside the shadow region of the carrier and the light guides (5) in the raised position have at least one diffuser (6) in the balancing out of the ambient light radiation.

14. The device according to claim 13, characterized in that the inclined orientation (β) amounts to 60° to 70°.

15. The device according to claim 13, characterized in that the angle (α) amounts to 90°.

* * * * *